(12) United States Patent
Miwa et al.

(10) Patent No.: US 9,202,668 B2
(45) Date of Patent: Dec. 1, 2015

(54) OBSERVATION SPECIMEN FOR USE IN ELECTRON MICROSCOPY, ELECTRON MICROSCOPY, ELECTRON MICROSCOPE, AND DEVICE FOR PRODUCING OBSERVATION SPECIMEN

(71) Applicant: Hitachi High-Technologies Corporation, Minato-ku, Tokyo (JP)

(72) Inventors: Takafumi Miwa, Tokyo (JP); Yoichi Ose, Tokyo (JP); Eiko Nakazawa, Tokyo (JP); Mami Konomi, Tokyo (JP); Shunya Watanabe, Tokyo (JP); Yoshinobu Kimura, Tokyo (JP); Natsuki Tsuno, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/354,917

(22) PCT Filed: Oct. 16, 2012

(86) PCT No.: PCT/JP2012/076704
§ 371 (c)(1),
(2) Date: Apr. 28, 2014

(87) PCT Pub. No.: WO2013/065475
PCT Pub. Date: May 10, 2013

(65) Prior Publication Data
US 2014/0264018 A1    Sep. 18, 2014

(30) Foreign Application Priority Data
Nov. 2, 2011   (JP) .................................. 2011-241040

(51) Int. Cl.
*G01N 23/00* (2006.01)
*H01J 37/26* (2006.01)
(Continued)

(52) U.S. Cl.
CPC ............... *H01J 37/261* (2013.01); *G01B 15/02* (2013.01); *G01N 23/00* (2013.01); *H01J 37/026* (2013.01);
(Continued)

(58) Field of Classification Search
CPC ..................................................... H01J 37/261
USPC ...................... 250/306, 307, 310, 311, 440.11
See application file for complete search history.

(56) References Cited

U.S. PATENT DOCUMENTS

2009/0140143 A1* 6/2009 Fukuda et al. ................. 250/311
2009/0173882 A1* 7/2009 Kuwabata et al. ............ 250/307
2012/0292507 A1* 11/2012 Morikawa et al. ............ 250/307

FOREIGN PATENT DOCUMENTS

JP       2000-195459 A    7/2000
JP       2000-338017 A   12/2000
WO     WO 2007/083756 A1  7/2007

OTHER PUBLICATIONS

Kanaya, K., et al., "Penetration and energy-loss theory of electrons in solid targets," J. Phys. D: Appl. Phys., vol. 5, 1972, pp. 43-58.

*Primary Examiner* — Constantine Hannaher
*Assistant Examiner* — Meenakshi Sahu
(74) *Attorney, Agent, or Firm* — Miles & Stockbridge PC

(57) ABSTRACT

The electrical charging by a primary electronic is inhibited to produce a clear edge contrast from an observation specimen (i.e., a specimen to be observed), whereby the shape of the surface of a sample can be measured with high accuracy. An observation specimen in which a liquid medium comprising an ionic liquid is formed in a thin-film-like or a webbing-film-like form on a sample is used. An electron microscopy using the observation specimen comprises: a step of measuring the thickness of a liquid medium comprising an ionic liquid on a sample; a step of controlling the conditions for irradiation with a primary electron on the basis of the thickness of the liquid medium comprising the ionic liquid; and a step of irradiating the sample with the primary electron under the above-mentioned primary electron irradiation conditions to form an image of the shape of the sample.

17 Claims, 15 Drawing Sheets

(51) Int. Cl.
*G01B 15/02* (2006.01)
*H01J 37/28* (2006.01)
*H01J 37/02* (2006.01)

(52) U.S. Cl.
CPC .......... *H01J 37/28* (2013.01); *H01J 2237/0044* (2013.01); *Y10T 428/24331* (2015.01); *Y10T 428/261* (2015.01)

F I G . 4
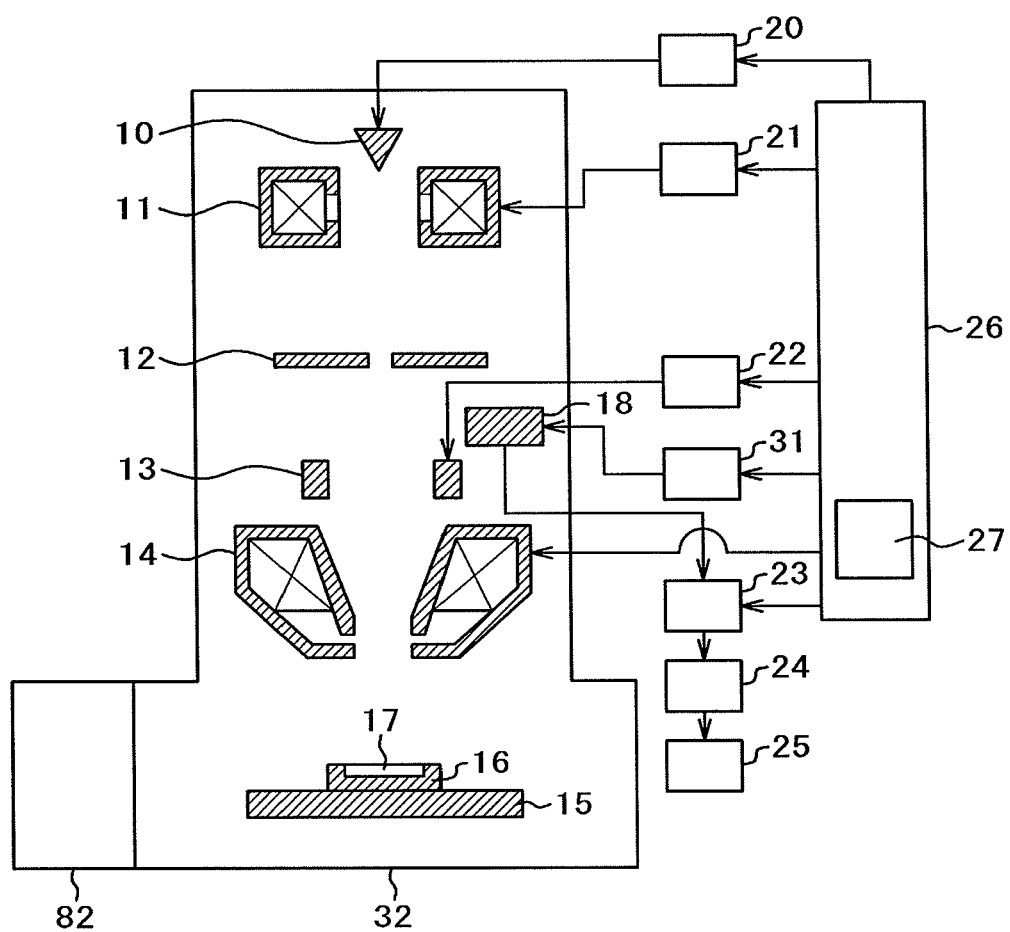

F I G . 17
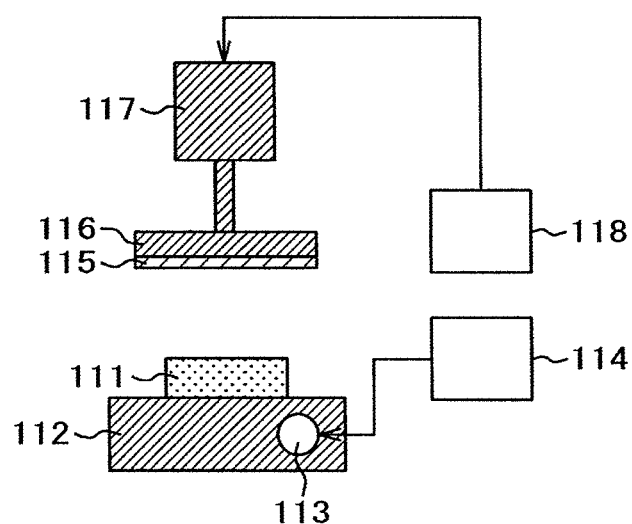

OBSERVATION SPECIMEN FOR USE IN ELECTRON MICROSCOPY, ELECTRON MICROSCOPY, ELECTRON MICROSCOPE, AND DEVICE FOR PRODUCING OBSERVATION SPECIMEN

TECHNICAL FIELD

The present invention relates to a microscope technology that observes a sample surface topology using electrons.

BACKGROUND ART

There is an electron microscope as an observation device for magnifying a sample surface topology. The operation of a scanning electron microscope (in the following, referred to as an SEM) is shown. Primary electrons accelerated by a voltage applied to an electron source are focused at an electron lens, and the focused primary electrons are scanned over a sample using a deflector. Secondary electrons emitted from the sample by irradiating the primary electrons are detected at a detector. Secondary electron signals are detected in synchronization with scanning signals to form an image. The amount of the secondary electrons emitted from the sample is varied depending on the sample surface topology.

In the case where a sample is an insulator, the sample surface inevitably becomes charged due to the irradiation of electrons. Charging due to the irradiation of electrons causes an image drift under observation, for example, to produce an image failure.

A method is known as a method for addressing an image failure caused by the charging in which an electric conductor is coated over the sample surface. Metals such as gold and platinum are used for the electric conductor. Moreover, Patent Literature 1 discloses a method in which a sample is applied with an ionic liquid hardly volatilized in a vacuum to provide electrical conductivity on the electron irradiation surface. Furthermore, Patent Literature 2 discloses a low-energy SEM that can provide stable observation using low-energy electrons even with charging.

CITATION LIST

Patent Literature

Patent Literature 1: International Publication No. WO2007/083756

Patent Literature 2: Japanese Patent Application Laid-Open Publication No. 2000-195459

SUMMARY OF INVENTION

Technical Problem

In these years, with a high resolution SEM, a low-energy SEM is used for inspection and measurement of a sample surface topology. However, even though low-energy electrons are used, the sample surface is charged. Thus, in the case where a sample surface topology is in a microstructure, an image failure due to charging such as the elimination of a contrast at the edge portion becomes a problem. In the case where a metal film is coated over an insulator sample in order to suppress an image failure in a low-energy SEM, a contrast caused by the grain boundary of the metal film is superposed on the shape contrast of the sample. Moreover, in the case where an ionic liquid is applied to the electron irradiation surface, the entire pattern surface is filled with the ionic liquid, and it is not enabled to observe the sample surface topology using a low-energy SEM.

It is an object of the present invention to provide an observation specimen for an electron microscopic method, an electron microscopic method, an electron microscope, and an observation specimen preparation device that address the problems above and suppress an image failure due to charging.

Solution to Problem

In order to address the problems above, in an observation specimen for an electron microscopic method according to the invention of the present application, a liquid medium including an ionic liquid on a sample is in a thin film shape or in a mesh film shape. The thin film or mesh film of the liquid medium including an ionic liquid of the observation specimen is coated according to a sample shape whether the film is along the sample surface topology or a low-energy primary electron can pass through the film thickness, so that a clear edge contrast can be obtained.

Here, in the observation specimen according to the invention of the present application, a film thickness of a portion to which the liquid medium including an ionic liquid is applied is one monolayer or more and 100 monolayers or less. One monolayer means the thickness of a single molecular layer of an ionic liquid.

Moreover, an electron microscopic method according to the invention of the present application includes the steps of: measuring a film thickness of a liquid medium including an ionic liquid in a thin film shape or in a mesh film shape on a sample; and controlling an irradiation condition for a primary electron based on the film thickness of the liquid medium including an ionic liquid. According to this method, the irradiation condition for a primary electron can be controlled according to the film thickness of the liquid medium including an ionic liquid, so that the edge contrast is improved.

Furthermore, the electron microscopic method according to the invention of the present application further includes the steps of: applying the liquid medium including an ionic liquid to an observation surface of the sample; and forming the liquid medium including an ionic liquid into a thin film. Generally, the film state of the applied liquid medium including an ionic liquid depends on the type of the ionic liquid and the material or shape of the sample. According to this method, the film thickness of the liquid medium including an ionic liquid can be controlled depending on the type of the ionic liquid or the sample.

Here, in the electron microscopic method according to the invention of the present application, an observation specimen is used that the liquid medium including an ionic liquid on the sample is in a thin film shape or in a mesh film shape.

Here, in the electron microscopic method according to the invention of the present application, the method may perform, for plural times, the steps of: applying the liquid medium including an ionic liquid to the observation surface of the sample; forming the liquid medium including an ionic liquid into a thin film; and measuring the film thickness of the liquid medium including an ionic liquid. According to this method, the liquid medium including an ionic liquid can be processed step by step until the liquid medium has a predetermined film thickness, so that the controllability of the film thickness of the liquid medium including an ionic liquid is improved.

Here, in the electron microscopic method according to the invention of the present application, the step of measuring the film thickness of the liquid medium including an ionic liquid may be the step of measuring the film thickness of the liquid medium including an ionic liquid from a primary electron acceleration voltage dependence of a secondary electron emission yield that is enabled to be analyzed using a pulsed primary electron. According to this method, the acceleration voltage at which a primary electron passes through the film of the liquid medium including an ionic liquid can be analyzed from a change in the secondary electron emission yield with respect to the acceleration voltage, and the film thickness of the liquid medium including an ionic liquid can be analyzed from the range of the primary electron at the acceleration voltage.

Here, in the electron microscopic method according to the invention of the present application, the step of measuring the film thickness of the liquid medium including an ionic liquid may be the step of measuring the film thickness of the liquid medium including an ionic liquid from a primary electron acceleration voltage dependence of a substrate current under the irradiation of primary electrons. Here, a displacement current that occurs due to electric charges stored when a primary electron passes to the sample is measured as a substrate current. According to this method, the acceleration voltage at which a primary electron passes through a film of the liquid medium including an ionic liquid can be analyzed by a change in the substrate current with respect to the acceleration voltage, and the film thickness of the liquid medium including an ionic liquid can be analyzed from the range of the primary electron at the acceleration voltage.

Moreover, an electron microscope according to the invention of the present application includes: an electron source configured to emit a primary electron; a sample holder configured to hold a sample; an exhaust chamber on which the sample holder is placed and configured to exhaust air; a lens system configured to focus the primary electron on the sample; a deflector configured to scan the primary electron; a detector configured to detect a secondary electron emitted from the sample by the primary electron; an image generating unit configured to form an image using the secondary electron; a sample chamber on which the sample holder is placed; a measuring mechanism configured to measure a film thickness of a liquid medium including an ionic liquid on the sample; and an irradiation condition control unit for the primary electron based on the film thickness of the liquid medium on the sample.

Here, in the electron microscope according to the invention of the present application, the measuring mechanism configured to measure a film thickness of the liquid medium including an ionic liquid may include: a pulse forming unit configured to form a pulse electron that the primary electron is pulsed; a secondary electron signal analyzing unit configured to analyze a secondary electron emission yield from a secondary electron signal that a secondary electron emitted from the sample by the pulse electron is detected at the detector; and a secondary electron emission yield analyzing unit configured to analyze an acceleration voltage at which the primary electron passes through a film of the liquid medium including an ionic liquid from an acceleration voltage dependence of the secondary electron emission yield and to analyze a film thickness from a range of the primary electron at the acceleration voltage.

Moreover, in the electron microscope according to the invention of the present application, the measuring mechanism configured to measure a film thickness of the liquid medium including an ionic liquid may include a substrate current measuring unit configured to measure a substrate current induced when the primary electron passes to the sample; and a substrate current analyzing unit configured to analyze an acceleration voltage at which the primary electron passes through a film of the liquid medium including an ionic liquid from an acceleration voltage dependence of the substrate current and to measure a film thickness from a range of the passing primary electron.

Here, in the electron microscope according to the invention of the present application, an applying unit configured to apply the liquid medium including an ionic liquid to an observation surface of the sample may be included on the sample holder or the sample chamber on which the sample is held.

Furthermore, in the electron microscope according to the invention of the present application, a mechanism configured to form the liquid medium including an ionic liquid on the sample into a thin film may be included on the sample holder or the sample chamber on which the sample is held.

In addition, an observation specimen preparation device that prepares the observation specimen according to the invention of the present application includes: an exhaust chamber; an exhaust mechanism; an applying unit configured to apply the liquid medium including an ionic liquid to an observation surface of a sample; a mechanism configured to form the liquid medium including an ionic liquid on the sample into a thin film; and a measuring mechanism configured to measure a film thickness of the liquid medium including an ionic liquid.

Here, the measuring mechanism configured to measure a film thickness of the liquid medium including an ionic liquid may include: an electron source configured to emit a primary electron; a substrate current measuring unit configured to measure a substrate current induced when the primary electron is irradiated to the sample; and a substrate current analyzing unit configured to analyze a primary electron acceleration voltage dependence of the substrate current.

Advantageous Effects of Invention

In accordance with the observation specimen, the electron microscopic method, the electron microscope, and the observation specimen preparation device according to the present invention, it is possible to suppress charging due to primary electrons, to obtain a clear edge contrast from the observation specimen, and to highly accurately measure a sample surface topology.

BRIEF DESCRIPTION OF DRAWINGS

FIG. 4 is a block diagram of an exemplary electron microscope according to the first embodiment of the present invention.

FIG. 17 is a block diagram of an exemplary observation specimen preparation device for an electron microscopic method according to a seventh embodiment of the present invention.

DESCRIPTION OF EMBODIMENTS

In the following, embodiments of the present invention will be described with reference to the drawings. However, the embodiments are merely examples for implementing the present invention, which will not limit the technical scope of the present invention.

First Embodiment

Figure 1A:
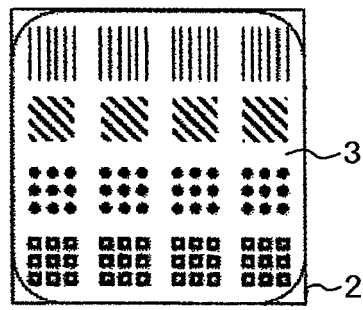
FIG. 1A is a top view of an exemplary observation specimen according to a first embodiment of the present invention.
Figure 1B:
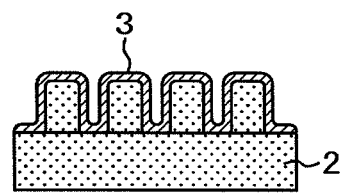
FIG. 1B is a cross sectional view of the exemplary observation specimen according to the first embodiment of the present invention.

FIG. 1A is a top view of an observation specimen that a liquid medium including an ionic liquid on a sample is in a thin film shape, and FIG. 1B is a cross sectional view of the observation specimen that the liquid medium including an ionic liquid is in a thin film shape. A sample 2 is a sample including groove patterns, and a liquid medium 3 including an ionic liquid is an ionic liquid in a thin film shape on the groove patterns. In the embodiment, an electron microscopic method will be described using the observation specimen that the liquid medium including an ionic liquid on the sample is in a thin film shape as illustrated in FIG. 1. It is noted that the ionic liquid for use in the present invention is 1-Butyl-3-methylimidazolium Tetrafluoroborate, 1-Ethyl-3-methylimidazolium bis (trifluoromethylsulfonyl) imide, and 1-Butyl-3-methylimidazolium bis (trifluoromethylsulfonyl) imide, for example. In the embodiment, a liquid medium including an ionic liquid was used in which the ionic liquid was diluted at 10% with pure water. In the embodiment, pure water was mixed in the ionic liquid. However, ethanol, methanol, acetone, and hexane, for example, may be mixed. Moreover, fine particles whose secondary electron emission yield is different from the secondary electron emission yield of the ionic liquid may be mixed in the ionic liquid in order to obtain a clear image contrast. The secondary electron emission yield means a rate that the number of secondary electrons emitted is divided by the number of primary electrons irradiated. The liquid medium including an ionic liquid means a liquid medium including an ionic liquid and a substance other than the ionic liquid. In the following, the ionic liquid refers to an ionic liquid or a liquid medium including an ionic liquid.

Figure 5A:
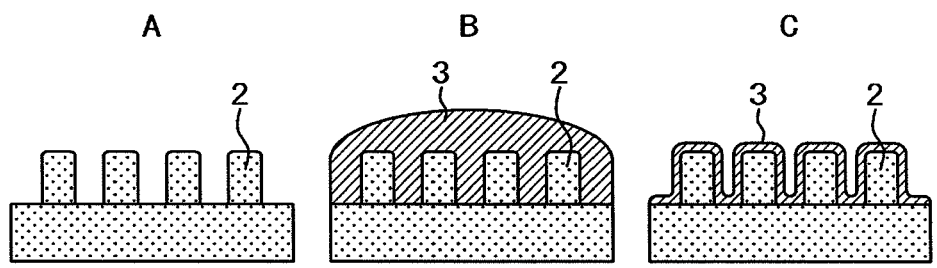
FIG. 5A is an illustration of the cross sectional structures of observation specimens.

FIG. 5A is the cross sectional structures of observation specimens used in the embodiment. In the embodiment, the sample 2 is an $SiO_2$ sample having line groove patterns. The sample 2 to which an ionic liquid is not applied (A in FIG. 5A), an observation specimen that an ionic liquid is dropped onto the sample 2 using a micropipet (B in FIG. 5A), and an observation specimen that an ionic liquid on the sample 2 is in a thin film shape in which the ionic liquid is applied to the sample 2 using a dip coater (C in FIG. 5A).

FIG. 4 is a block diagram of an electron microscope according to the embodiment. The electron microscope is configured of an electro-optical system, a stage system, a control system, an image processing system, a manipulation interface 27, a sample chamber 32, and an exhaust chamber 82. The electro-optical system is configured of an electron source 10, a condenser lens 11, a diaphragm 12, a deflector 13, an objective lens 14, and a detector 18. The stage system is configured of a sample stage 15, a sample holder 16, and a sample 17. The control system is configured of an electron source control unit 20, a condenser lens control unit 21, a deflection signal control unit 22, a detector control unit 31, and an SEM control unit 26. The image processing system is configured of a detection signal processing unit 23, an image generating unit 24, and an image display unit 25.

The irradiation conditions controlled in the embodiment are the acceleration voltage of primary electrons, an irradiation electric current, and a primary electron scanning speed. The acceleration voltage is controlled using a voltage applied to the electron source 10 by the electron source control unit 20, and the irradiation electric current is controlled using an excitation current applied to the condenser lens 11 by the condenser lens control unit 21. Moreover, the scanning speed is controlled by a deflection signal from the deflection signal control unit 22 to the deflector 13.

Figure 5B:
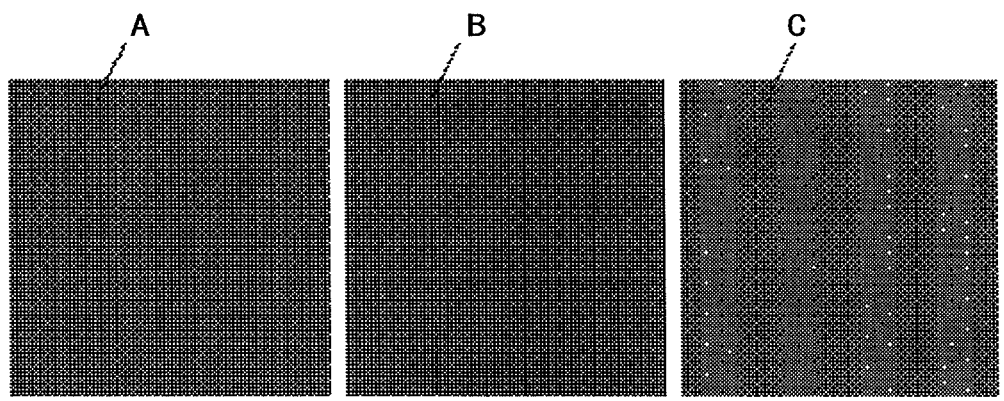
FIG. 5B is a diagram of SEM images of the observation specimens.

FIG. 5B is SEM images acquired at an acceleration voltage of 1.0 kV, an irradiation electric current of 8 pA, and a primary electron scanning speed of 300 nm/µs. A in FIG. 5B is an SEM image of the sample 2 to which the ionic liquid is not applied, in which pattern portions become dark due to charging to cause shading. On the other hand, B in FIG. 5B is an SEM image of the observation specimen that the ionic liquid is dropped onto the sample 2 using the micropipet. In the case where the ionic liquid is applied using the micropipet, the ionic liquid does not take a thin film shape, and primary electrons are not enabled to pass through the ionic liquid, and thus it is not enabled to recognize patterns. C in FIG. 5B is an SEM image of the observation specimen that the ionic liquid on the sample 2 is in a thin film shape. Shading on pattern portions is suppressed, and patterns can also be recognized.

Figure 5C:
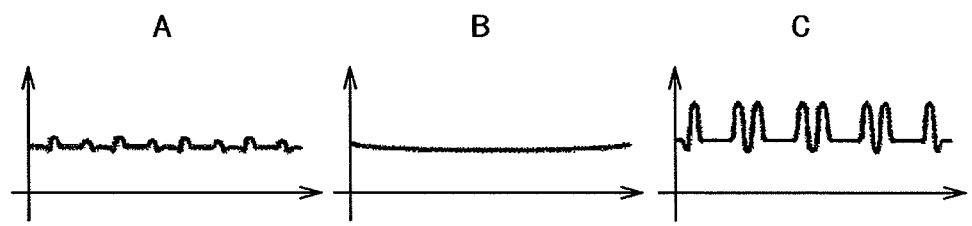
FIG. 5C is a diagram of the profiles of image lightness of the observation specimens.

FIG. 5C is the profiles of image lightness analyzed in the direction across groove patterns. A portion showing the maximum image lightness corresponds to the edge portion of a groove. In A in FIG. 5C, the signal of the maximum portion corresponding to the edge portion is weak, and the edge contrast is small. Moreover, B in FIG. 5C, it is difficult to recognize the profile of the edge portion. On the other hand, in C in FIG. 5C, the signal of the maximum portion is strong, and a clear edge contrast is obtained. In accordance with the electron microscopic method according to the embodiment, it is possible to improve an edge contrast expressing the sample shape using the observation specimen that an ionic liquid on the sample is in a thin film shape.

Second Embodiment

In this embodiment, an electron microscopic method will be described in which the film thickness of an ionic liquid is measured and the irradiation conditions for the primary electrons are controlled based on the measured film thickness. In the embodiment, the observation specimen was used that the ionic liquid on the sample is in a thin film shape in C in FIG. 5A shown in the first embodiment.

In consideration of the film thickness of the ionic liquid and the range of low-energy primary electrons, the irradiation conditions for the primary electrons are controlled. Here, the range of electrons means the length of electrons passing through the inside of a substance. As described in a reference (K. Kanaya, S. Okayama, J. Phys. D. Appl. Phys. 5, 43 (1972)), a range R (μm) of the primary electrons is expressed by Equation 1.

$$R = \frac{0.0276 (eV)^{5/3} A}{\rho^{8/9} Z}$$ [Equation 1]

ρ (g/cm³) is the density of a substance through which electrons pass, Z is an atomic number, A (g/mol) is an atomic weight, V (kV) is the acceleration voltage of the primary electrons, and e is an elementary electric charge. Equation 1 expresses that the range of the primary electrons depends on the acceleration voltage of the primary electrons as well as depends on the density of a substance and the atomic weight. Here, since the thickness of a single molecular layer of an ionic liquid depends on the density and molecular weight of the ionic liquid, the range of the primary electrons can be prescribed by a monolayer in a unit of the thickness of a single molecular layer (in the following, the thickness of a single molecular layer is referred to as a monolayer). It is important to adjust the acceleration voltage of the primary electrons based on the range of the primary electrons prescribed by a monolayer and the film thickness of the ionic liquid. Moreover, even in the case where the irradiation conditions are determined and the film thickness of the ionic liquid can be adjusted, it is important to adjust the film thickness of the ionic liquid in consideration of the range of the primary electrons.

The acceleration voltage of the primary electrons ranges from a voltage of 0.1 to 1.5 kV, for example. In the ionic liquid used in the embodiment, the acceleration voltage of the primary electrons passing through the film thickness of 100 monolayers is a voltage of 1.5 kV, and the acceleration voltage of the primary electrons passing through the film thickness of one monolayer is a voltage of 0.1 kV. In the estimation from the density, the molecular weight, and the composition, one monolayer of a typical ionic liquid was a thickness of 1 nm.

The film thickness of a portion to which the liquid medium including an ionic liquid is applied in the observation specimen is to be one monolayer or more and 100 monolayers or less, for example.

Figure 3A:
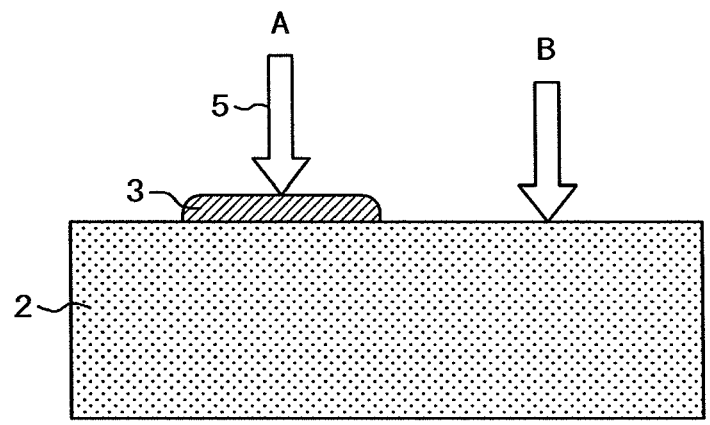
FIG. 3A is an illustration of the presence or absence of a liquid medium including an ionic liquid on a sample.
Figure 3B:
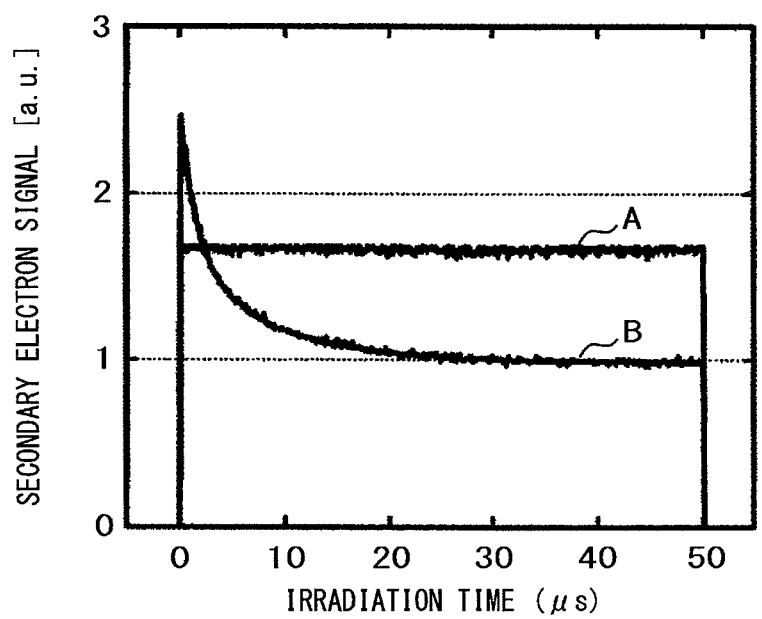
FIG. 3B is a diagram of the time variations of secondary electron signals corresponding to the presence or absence of a liquid medium including an ionic liquid on a sample.

FIG. 3A is a sample 2 and an observation specimen that the ionic liquid on the sample 2 is in a thin film shape. In the embodiment, the sample 2 is an insulator. Moreover, FIG. 3B is the time variations of secondary electron signals emitted when low-energy primary electrons are irradiated to the sample 2 and the observation specimen that the ionic liquid on the sample 2 is in a thin film shape. As illustrated in B in FIG. 3B, when low-energy primary electrons are irradiated to the sample 2, secondary electrons are emitted greater than the number of the primary electrons irradiated, and the sample surface is positively charged. At this time, since the amount of the secondary electrons emitted is reduced due to the positively charged surface, the secondary electron signal is attenuated immediately after the primary electrons are irradiated. On the other hand, as illustrated in A in FIG. 3A, in the observation specimen that the ionic liquid on the sample 2 is in a thin film shape, since charging in the irradiation region of the primary electrons is suppressed, the secondary electron signal is not attenuated under the irradiation of the primary electrons, and takes a constant value. Thus, even in the case where the ionic liquid is in a thin film shape, it is shown that the effect of suppressing charging is exerted.

A, B, and C in FIGS. 5B and 5C are images and the profiles of image lightness in which the sample 2 with patterns, the observation specimen including an ionic liquid on the sample 2, and the observation specimen that the ionic liquid on the sample 2 is in a thin film shape are observed using low-energy primary electrons. As illustrated in A in FIG. 5B, when no ionic liquid is present, the pattern portion is in a low contrast due to the charged surface. As illustrated in B in FIG. 5B, when the ionic liquid is not a thin film, the pattern portion is filled with the ionic liquid, and the edge contrast is eliminated. As illustrated in C in FIG. 5B, when the ionic liquid is in a thin film shape, a high contrast is obtained from the pattern portion. Moreover, as illustrated in A in FIG. 5C, when no ionic liquid is present, the signal of the edge portion is reduced due to the charged sample, and the profile of image lightness is in asymmetry. On the other hand, as illustrated in C in FIG. 5C, when the ionic liquid is in a thin film shape, the profile of image lightness is in symmetry, and such a contrast is obtained in which the edge portion of the sample 2 is more highlighted. When the observation specimen includes an ionic liquid in a thin film shape on the sample, the edge contrast of the sample 2 is obtained even using low-energy electrons while the effect of suppressing charging is provided.

Figure 6:
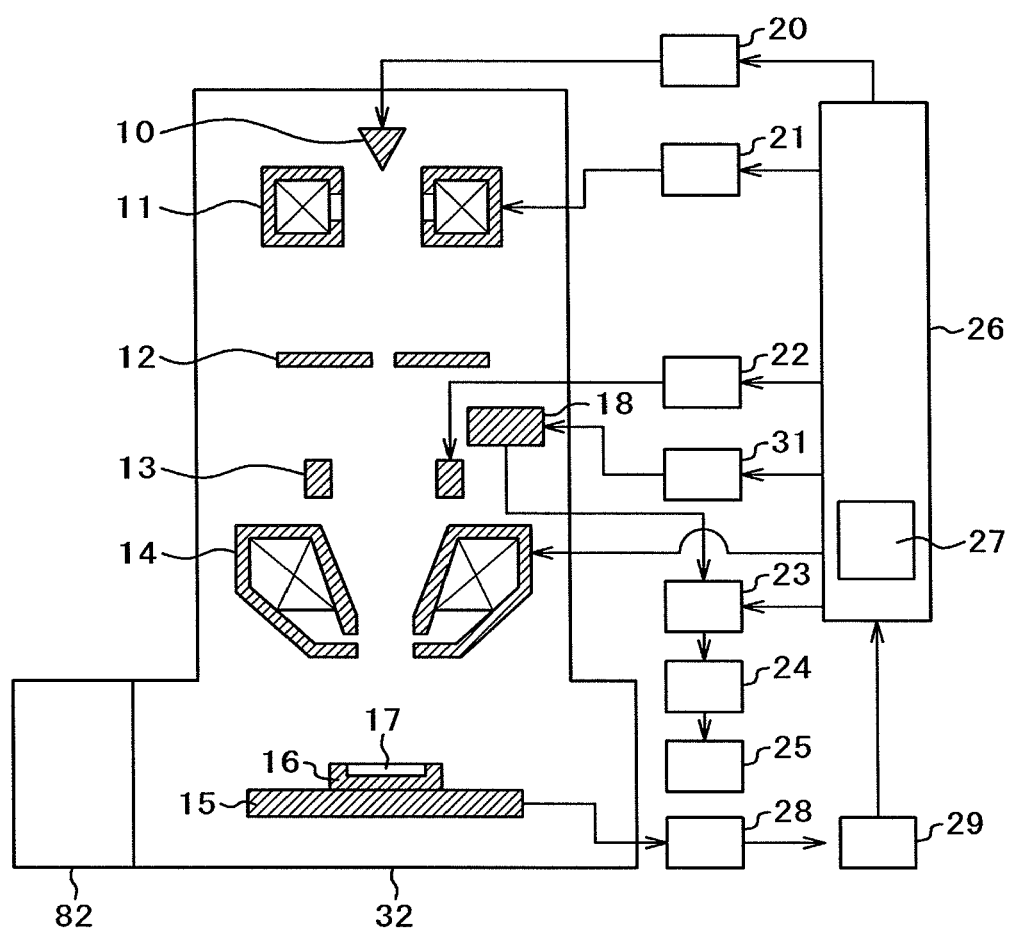
FIG. 6 is a block diagram of an exemplary electron microscope according to a second embodiment of the present invention.

FIG. 6 is a block diagram of an electron microscope according to the embodiment. The electron microscope is configured of an electro-optical system, a stage system, a control system, an image processing system, a manipulation interface 27, a sample chamber 32, an exhaust chamber 82, and a substrate current measurement system. The substrate current is an electric current carried from the observation specimen to the stage system (a sample holder 16) by irradiating primary electrons. The electro-optical system is configured of an electron source 10, a condenser lens 11, a diaphragm 12, a deflector 13, an objective lens 14, and a detector 18. The stage system is configured of a sample stage 15, the sample holder 16, and a sample 17. The control system is configured of an electron source control unit 20, a condenser lens control unit 21, a deflection signal control unit 22, a detector control unit 31, and an SEM control unit 26. The image processing system is configured of a detection signal processing unit 23, an image generating unit 24, and an image display unit 25. The substrate current measurement system is configured of an ammeter 28 and a substrate current analyzing unit 29.

Figure 7:
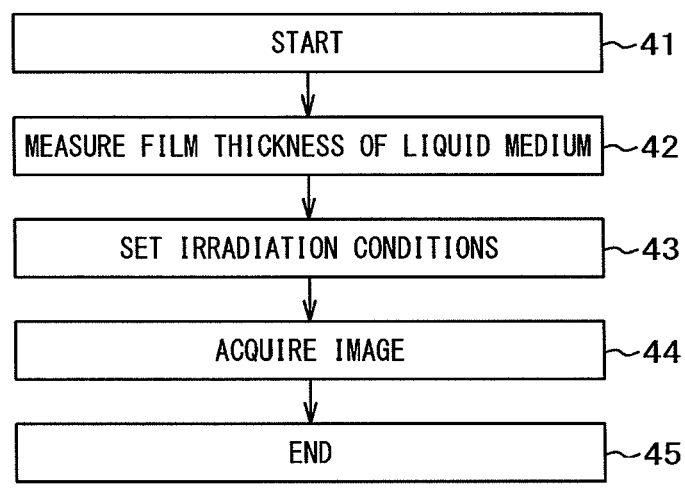
FIG. 7 is a diagram of an exemplary flowchart of an electron microscopic method according to the second embodiment of the present invention.
Figure 8A:
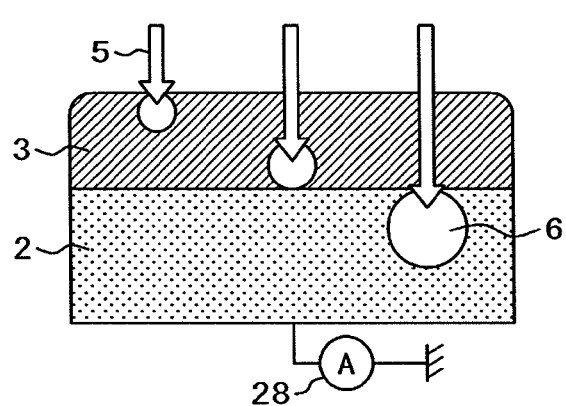
FIG. 8A is an illustration of the relationship between the acceleration voltage and range of primary electrons according to the second embodiment.
Figure 8B:
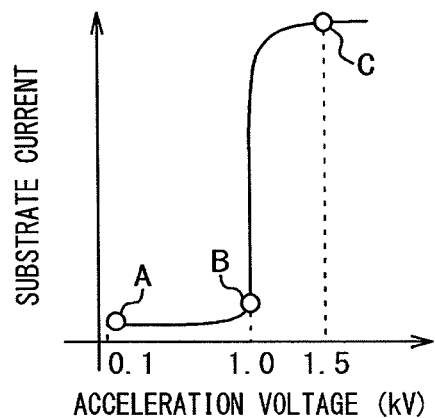
FIG. 8B is an illustration of the relationship between the acceleration voltage of primary electron and the substrate current according to the second embodiment.

FIG. 7 is a flowchart of the electron microscopic method. The electron microscopic method according to the embodiment will be described with reference to the flowchart in FIG. 7. First, the film thickness of the ionic liquid of the observation specimen is measured (Step 42). In the embodiment, a substrate current was measured under the irradiation of the primary electrons using the electron microscope illustrated in FIG. 6, and the film thickness of the ionic liquid was analyzed. Here, a displacement current induced by electric charges stored on the sample under the irradiation of the primary electrons can be measured as a substrate current. First, the electron source control unit 20 controls the acceleration voltage of the primary electrons using the voltage applied to the electron source 10, and changes the acceleration voltage, and substrate currents at the individual acceleration voltages are measured at the ammeter 28. FIG. 8A is a schematic diagram of the relationship between the acceleration voltage and range of the primary electrons. When the acceleration voltage of the primary electrons is increased as in A, B, and C, the range of a primary electron 5 is increased. When the range of the primary electron is the film thickness of a liquid medium 3 including an ionic liquid or more (C in FIG. 8A), the primary electron reaches the sample 2, and electric charges are stored on the sample. At this time, a displacement current occurs due to stored charges, and can be measured as a substrate current. FIG. 8B is changes in the substrate current when the acceleration voltage of the primary electrons is changed from a voltage of 0.1 kV to a voltage of 1.5 kV. It is shown from FIG. 8B that the substrate current is suddenly increased at an acceleration voltage of 1.0 kV. The acceleration voltage when this substrate current is suddenly increased is an acceleration voltage at which the primary electron passes through the film thickness. As a result that the range is analyzed by Equation 1, since the range at an acceleration voltage of 1.0 kV is 60 monolayers, the film thickness of the ionic liquid is 60 monolayers. The process step of analyzing the acceleration voltage dependence of the substrate current described in the embodiment is processed at the substrate current analyzing unit 29, and the film thickness can be automatically obtained.

Next, the irradiation conditions for the primary electrons are controlled based on the film thickness with reference to the flowchart in FIG. 7 (Step 43). In the embodiment, in order to detect secondary electrons from the sample, the acceleration voltage was controlled at a voltage of 1.2 kV in such a way that the range of the primary electrons is longer than 60 monolayers. At this time, the primary electrons pass through the ionic liquid thin film, and reach the sample. Thus, in order to restrict the number of electrons irradiated to the sample in consideration of the sample damage, the irradiation electric current was controlled at 5 pA, and the scanning speed was controlled at 300 nm/μs.

Lastly, an image is acquired under the set irradiation conditions for the primary electrons based on the flowchart in FIG. 7, and the image is displayed on the image display unit 25 (Step 44).

Figure 19:
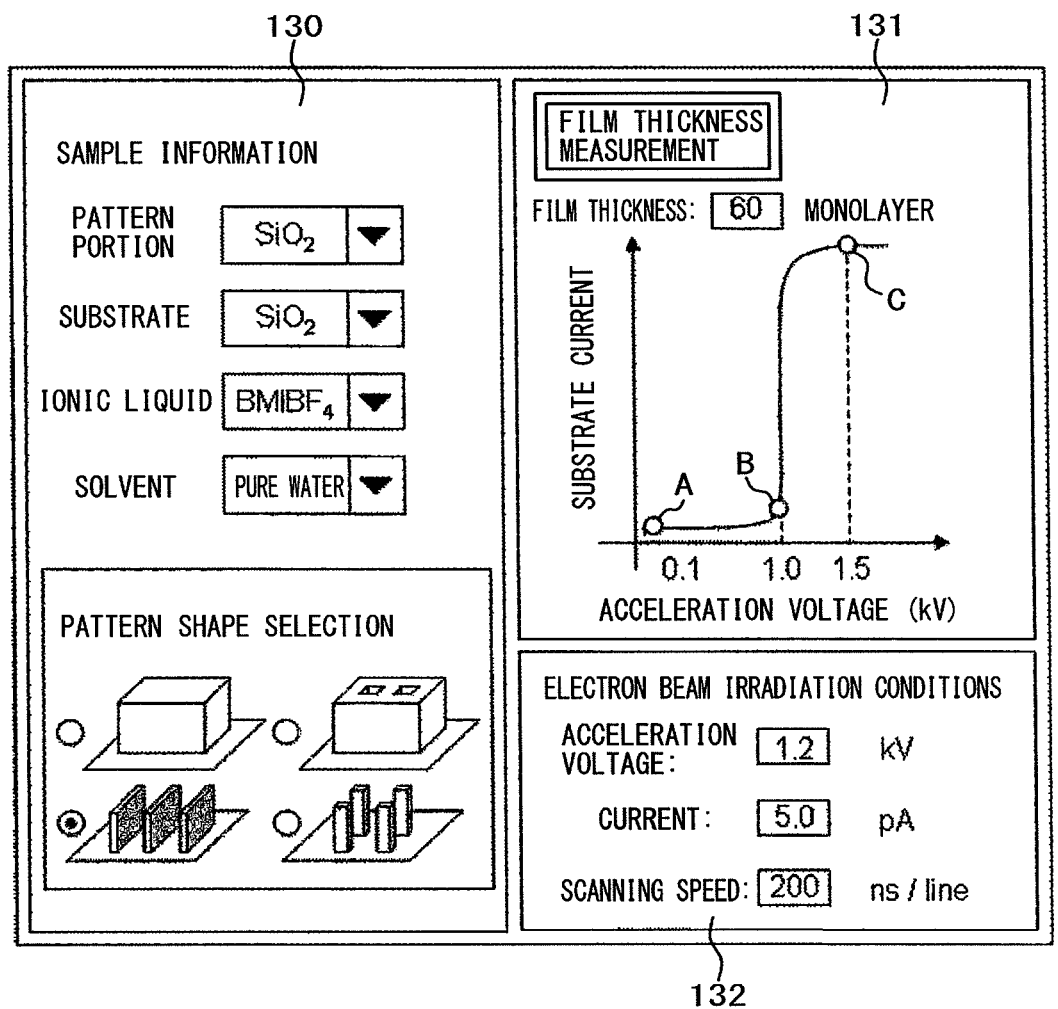
FIG. 19 is a diagram of an exemplary GUI for setting irradiation conditions for primary electrons according to the present invention.

FIG. 19 is a graphical user interface (in the following, referred to as a GUI) that sets the irradiation conditions for the primary electrons according to the embodiment. The GUI in FIG. 19 is displayed on the monitor of the manipulation interface 27. On a window 130, information about a sample and an ionic liquid inputted to the SEM control unit 26 are displayed. On a window 131, the acceleration voltage dependence of the substrate current of the observation specimen and the film thickness of the ionic liquid are displayed. On a window 132, the irradiation conditions for the primary electrons corresponding to the film thickness of the ionic liquid are displayed.

Figure 9A:
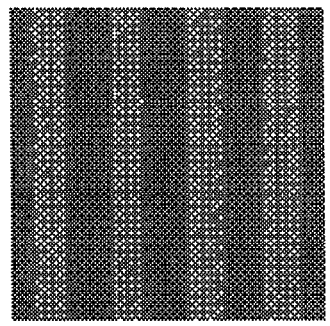
FIG. 9A is a diagram of an SEM image obtained through an electron microscopic method according to the second embodiment.
Figure 9B:
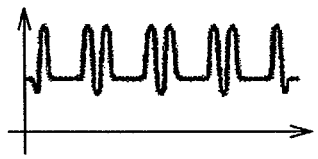
FIG. 9B is an illustration of the profile of image lightness obtained through the electron microscopic method according to the second embodiment.

FIG. 9A is an image obtained by observing the observation specimen, and FIG. 9B is the profile of image lightness analyzed in the direction across groove patterns according to the embodiment. The maximum value of image lightness expressing the edge portion of the pattern is great, and a clear edge contrast can be obtained. In accordance with the electron microscopic method according to the embodiment, the film thickness of the ionic liquid thin film is measured, and the optimum irradiation conditions can be set, so that it is possible to improve an edge contrast expressing the sample shape.

Third Embodiment

In the embodiment, an electron microscopic method will be described using an observation specimen in which an ionic liquid is applied to a sample and then formed into a thin film. In the embodiment, a resist sample having line groove patterns was used.

Figure 10:
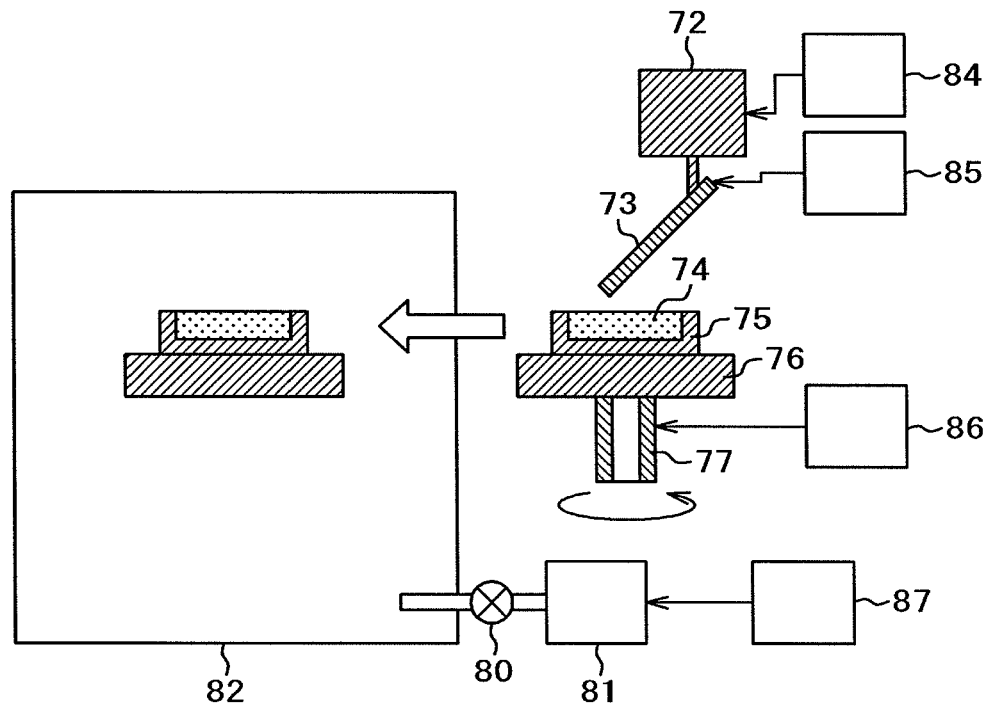
FIG. 10 is a block diagram of an exemplary observation specimen preparation device for an electron microscopic method according to a third embodiment of the present invention.

FIG. 10 is a block diagram of an observation specimen preparation device for an electron microscopic method according to the embodiment. Here, the observation specimen preparation device is a device that applies an ionic liquid to a sample and prepares an observation specimen, including an ionic liquid adjusting unit 72 that mixes an ionic liquid with a substance different from the ionic liquid, an ionic liquid discharging unit 73, a sample 74, a sample holder 75, a sample holding unit 76, a sample holding unit rotating mechanism 77, a valve 80, an exhaust mechanism 81, an exhaust chamber 82, and a control system. The control system is configured of an ionic liquid adjustment control unit 84, a discharge control unit 85, a rotation control unit 86, and an exhaust control unit 87. Although the observation specimen preparation device for an electron microscopic method is a part of an electron microscope, the device may be independent of the electron microscope. An electron microscope according to the embodiment is in the configuration similar to FIG. 4.

Figure 11:
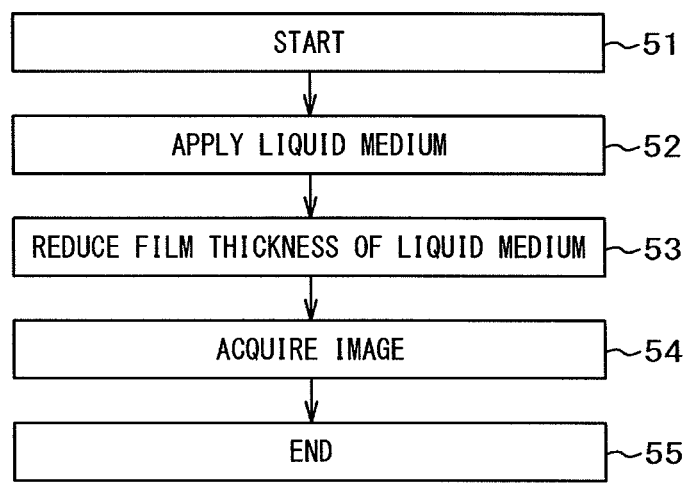
FIG. 11 is a diagram of an exemplary flowchart of an electron microscopic method according to the third embodiment of the present invention.

FIG. 11 is a flowchart of the electron microscopic method. The electron microscopic method according to the embodiment will be described with reference to the flowchart in FIG. 11. First, an ionic liquid is applied to the sample 74 (Step 52). In the embodiment, the ionic liquid was applied using the observation specimen preparation device in FIG. 10. First, an ionic liquid adjusted at the ionic liquid adjusting unit 72 is controlled by the discharge control unit 85 and discharged from the discharging unit 73, and the ionic liquid is applied to the sample 74. In the embodiment, pure water was mixed in the ionic liquid as a solvent, and the ionic liquid whose viscosity was 20 mPa·s was discharged onto the sample.

Subsequently, based on the flowchart in FIG. 11, the applied ionic liquid is formed into a thin film (Step 53). In the embodiment, the ionic liquid was formed into a thin film using the observation specimen preparation device in FIG. 10 by rotating the sample holding unit 76 using the sample holding unit rotating mechanism 77. The rotation control unit 86 controlled the rotation speed and rotation time in such a way that the sample holding unit 76 was rotated at 500 rpm for 10 seconds and then rotated at 3,000 rpm for 60 seconds. Subsequently, the sample 74 was put into the exhaust chamber 82 for vacuum exhaust. When the ionic liquid includes a substance that is vaporized under a vacuum, the substance that is vaporized under a vacuum is vaporized by vacuum exhaust, so that the ionic liquid can be formed into a thin film. In the embodiment, vacuum exhaust was performed until the pressure of the exhaust chamber 82 reached a pressure of $1 \times 10^{-4}$ Pa, which is almost the same vacuum degree in electron microscopic observation. Here, in the embodiment, the ionic liquid is applied and then vacuum exhaust is performed. However, it may be fine that an ionic liquid is applied under a vacuum and the process of forming a thin film is performed.

Lastly, based on the flowchart in FIG. 11, an image of the observation specimen is acquired (Step 54). In the embodiment, the acceleration voltage of the primary electrons is a voltage of 0.1 kV, the electric current is 5 pA, and the scanning speed is 200 nm/μs.

The image obtained by observing the prepared observation specimen according to the embodiment is similar to the image in C in FIG. 5B, and the profile of image lightness analyzed in the direction across groove patterns is similar to the profile in C in FIG. 5C. The maximum value of image lightness expressing the edge portion of the pattern is great, and a clear edge contrast can be obtained. In accordance with the electron microscopic method according to the embodiment, the film thickness of the ionic liquid thin film can be controlled, and the image can be acquired, so that it is possible to improve an edge contrast expressing the sample shape.

Fourth Embodiment

In the embodiment, an electron microscopic method will be described in which the irradiation conditions for the primary electrons are set, it is determined whether the film thickness is an appropriate film thickness to the set irradiation conditions for the primary electrons, and then an image is acquired. In the embodiment, the observation specimen described in the third embodiment was used.

Figure 12:
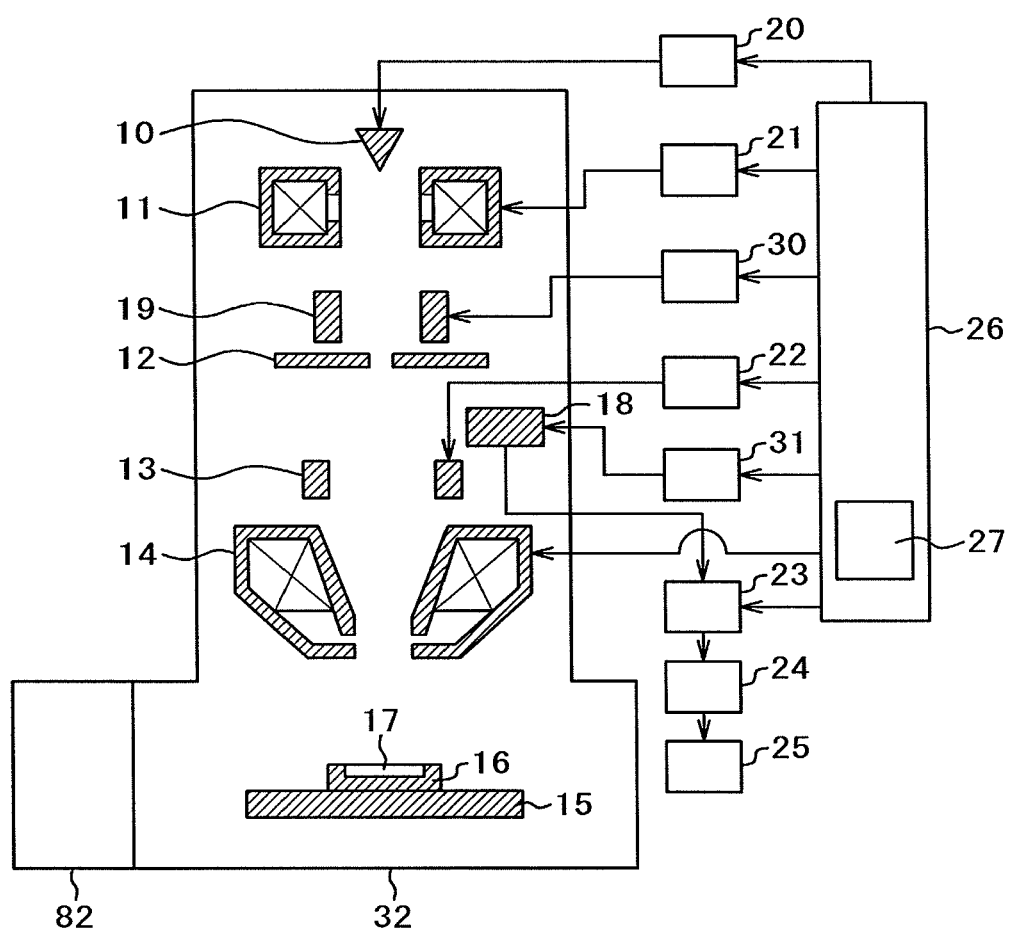
FIG. 12 is a block diagram of an exemplary electron microscope according to a fourth embodiment of the present invention.

FIG. 12 is a block diagram of an electron microscope according to the embodiment. The electron microscope is configured of an electro-optical system, a stage system, a control system, an image processing system, a manipulation interface 27, a sample chamber 32, and an exhaust chamber 82. The electro-optical system is configured of an electron source 10, a condenser lens 11, a diaphragm 12, a deflector 13, an objective lens 14, a detector 18, and a pulse forming unit 19. The stage system is configured of a sample stage 15, a sample holder 16, and a sample 17. The control system is configured of an electron source control unit 20, a condenser lens control unit 21, a deflection signal control unit 22, a detector control unit 31, an SEM control unit 26, and a pulse control unit 30. The image processing system is configured of a detection signal processing unit 23, an image generating unit 24, and an image display unit 25.

Figure 13:
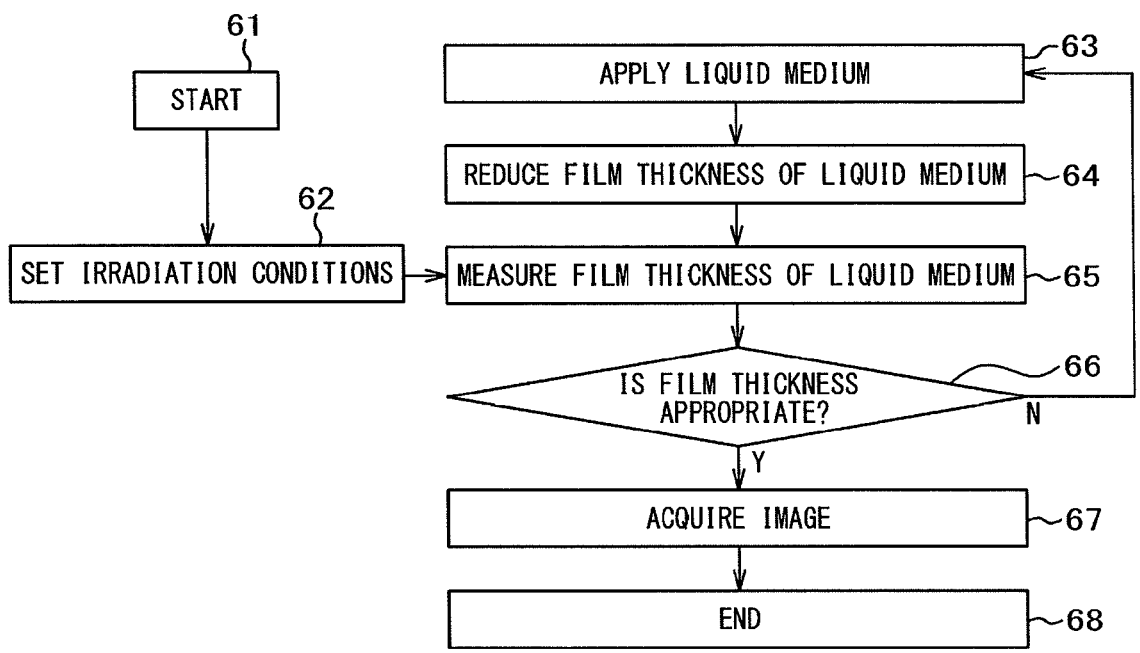
FIG. 13 is a diagram of an exemplary flowchart of an electron microscopic method according to the fourth embodiment of the present invention.

FIG. 13 is a flowchart of the electron microscopic method. The electron microscopic method according to the embodiment will be described with reference to the flowchart in FIG. 13. First, the irradiation conditions for the primary electrons are set (Step 62). In the embodiment, the electron microscopic method is performed using the electron microscope in FIG. 12. Here, the irradiation condition for the primary electrons was an acceleration voltage of 0.3 kV at which the secondary electron emission yield is high. In the embodiment, in order to prevent the sample from being damaged due to the direct irradiation of the primary electrons to a resist, a thin film is formed in such a way that the film thickness of an ionic liquid is thicker than the range of the primary electrons at a voltage of 0.3 keV and the ionic liquid film reflects the sample surface topology. Here, since the primary electrons do not pass through the ionic liquid film, the irradiation conditions for the primary electrons were controlled in which the irradiation electric current was 20 pA and the scanning speed was 100 nm/μs at which the SN ratio of an image is high.

Subsequently, the film thickness of the ionic liquid of the observation specimen was measured based on the flowchart in FIG. 13 (Step 65). The observation specimen used in the embodiment is the observation specimen described in the third embodiment. In the embodiment, the film thickness of the ionic liquid was analyzed by measuring the secondary electron emission yield using pulse electrons with the electron microscope in FIG. 12. Here, a method for measuring the secondary electron emission yield will be described. When low-energy primary electrons are irradiated, the insulator is positively charged, and the number of the secondary electrons to be emitted is reduced. When the number of the primary electrons irradiated is matched with the number of the secondary electrons emitted, the secondary electron emission yield becomes one in the stationary state. In other words, the secondary electron emission yield of one corresponds to the strength of the secondary electron signal in which the pulse electrons formed at the pulse forming unit 19 are irradiated and secondary electrons detected at the detector 18 are reduced under the irradiation of the primary electrons and become stationary. The strength of the secondary electron signal when the primary electrons are irradiated is divided by the strength of the secondary electron signal in the stationary state, and the secondary electron emission yield is obtained.

Figure 14:
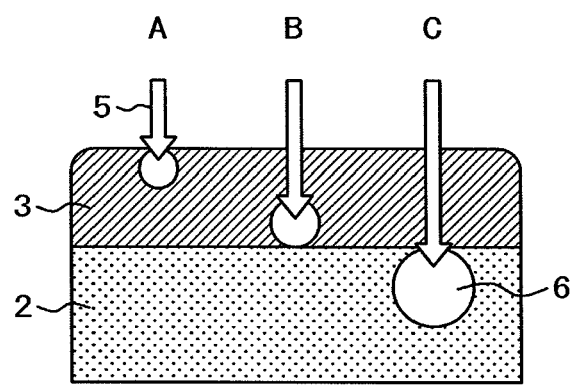
FIG. 14 is an illustration of the relationship between the acceleration voltage of primary electrons and the secondary electron emission yield.
Figure 14:
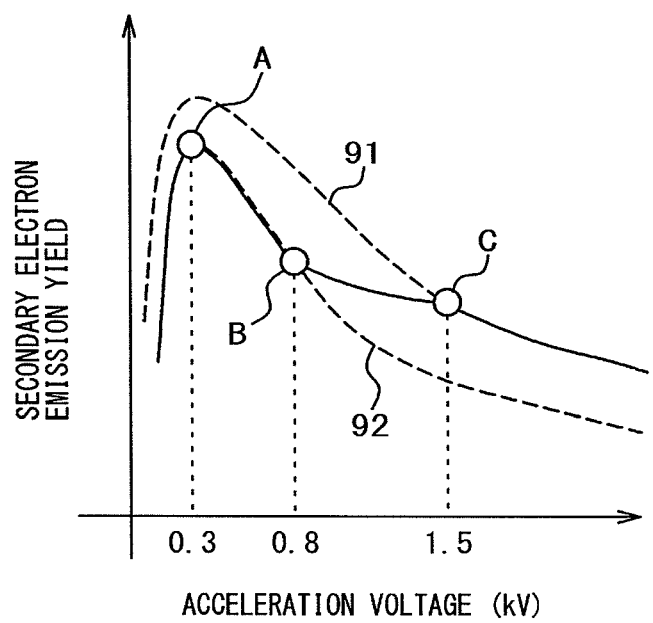

FIG. 14 is the acceleration voltage dependence of the secondary electron emission yield of the observation specimen used in the embodiment. In the embodiment, since it is necessary to compare the secondary electron emission yield of the ionic liquid with the secondary electron emission yield of the resist, the acceleration voltage dependences of the secondary electron emission yields of the ionic liquid and the resist were complied into a database. FIG. 14 is the secondary electron emission yield of the observation specimen as well as the acceleration voltage dependence of a secondary electron emission yield 91 of the resist and the acceleration voltage dependence of a secondary electron emission yield 92 of the ionic liquid called from the database. The secondary electron emission yield of the observation specimen was matched with the acceleration voltage dependence of the secondary electron emission yield 92 of the ionic liquid at an acceleration voltage of 0.8 kV or less, and was almost matched with the acceleration voltage dependence of the secondary electron emission yield 91 of the resist at an acceleration voltage of 1.5 kV or more. On the other hand, at the acceleration voltage ranging from a voltage of 0.8 kV to a voltage of 1.5 kV, the secondary electron emission yield of the observation specimen takes the median value between the acceleration voltage dependence of the secondary electron emission yield 92 of the ionic liquid and the acceleration voltage dependence of the secondary electron emission yield 91 of the resist. Thus, it can be determined from FIG. 14 that the ionic liquid is passed at an acceleration voltage of 0.8 kV. As a result that the range was analyzed from Equation 1, since the range at an acceleration voltage of 0.8 kV is 50 monolayers, the film thickness of the ionic liquid is 50 monolayers. Here, in the ionic liquid used in the embodiment, the thickness of one monolayer is 0.5 nm.

Subsequently, it was determined whether the film thickness of the ionic liquid is appropriate based on the flowchart in FIG. 13 (Step 66). Since the range at a voltage of 0.3 kV, which is the acceleration voltage according to the embodiment, is 20 monolayers, and is the film thickness (50 monolayers) measured in the embodiment or less, it was determined that the film thickness is appropriate. Here, in the case where the film thickness is thinner than 20 monolayers, the ionic liquid is again applied, the ionic liquid is processed into a thin film, the film thickness is measured (Steps 63, 64, and 65), and the processes are repeated until a predetermined film thickness is obtained.

Lastly, based on the flowchart in FIG. 13, an image is acquired under the set irradiation condition for the primary electrons, and the image is displayed on the image display unit 25 (Step 67).

An image obtained by observing the prepared observation specimen according to the embodiment is similar to FIG. 9A, and the profile of image lightness analyzed in the direction across groove patterns is similar to FIG. 9B. The maximum value of image lightness expressing the edge portion of the pattern is great, and a clear edge contrast can be obtained. In accordance with the electron microscopic method according to the embodiment, the film thickness of the ionic liquid thin film can be highly accurately controlled, so that the edge contrast reflecting the sample shape can be improved.

Fifth Embodiment

Figure 2A:
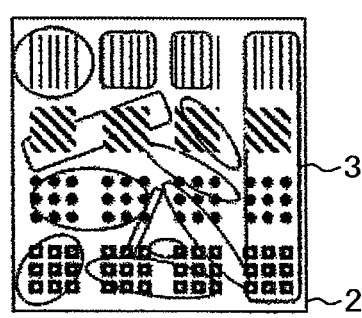
FIG. 2A is a top view of an exemplary observation specimen according to a fifth embodiment of the present invention.
Figure 2B:
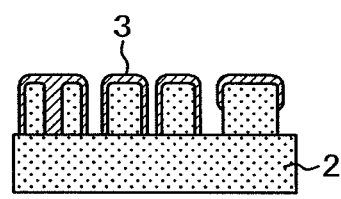
FIG. 2B is a cross sectional view of the exemplary observation specimen according to the fifth embodiment of the present invention.

FIG. 2A is a top view of an observation specimen that an ionic liquid is in a mesh film shape, and FIG. 2B is a cross sectional view of the observation specimen that the ionic liquid is in a mesh film shape. In this embodiment, an electron microscopic method will be described using an observation specimen that an ionic liquid is in a mesh film shape as illustrated in FIG. 2. In the embodiment, the configuration of the electron microscope illustrated in FIG. 12 was used. Moreover, in the embodiment, an $SiO_2$ sample having groove patterns of different pitches and sizes wads used. A hydrophobic ionic liquid was used, and was applied to the sample pattern surface using a dip coater. Since the wettability between the ionic liquid and the sample is varied depending on the pattern pitch and pattern size of the sample, the state of an ionic liquid film is different for individual patterns.

Figure 15A:
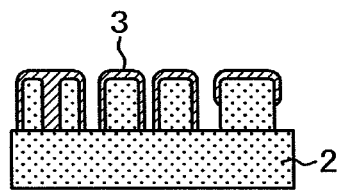
FIG. 15A is an illustration of the structure of an observation specimen for use in the fifth embodiment.
Figure 15B:
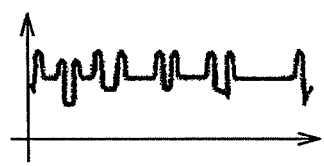
FIG. 15B is a diagram of the profile of image lightness of the observation specimen for use in the fifth embodiment.

FIG. 15A is the structure of the observation specimen used in the embodiment. As illustrated in FIG. 15A, in the observation specimen, the state of an ionic liquid film is varied depending on the pattern pitch and pattern size of the sample. FIG. 15B is the profile of image lightness analyzed in the direction across groove patterns of an SEM image of this observation specimen acquired at an acceleration voltage of 1.0 kV, an irradiation electric current of 8 pA, and a scanning speed of 300 nm/µs. As illustrated in FIG. 15B, contrasts are observed corresponding to the pattern pitch and pattern size of the sample. In accordance with the electron microscopic method according to the embodiment, it is possible to highly accurately measure the sample shape from the observation specimen including an ionic liquid.

Sixth Embodiment

In this embodiment, an observation specimen preparation device for an electron microscopic method will be described, which is in another configuration different from the method described in the third embodiment.

Figure 16:
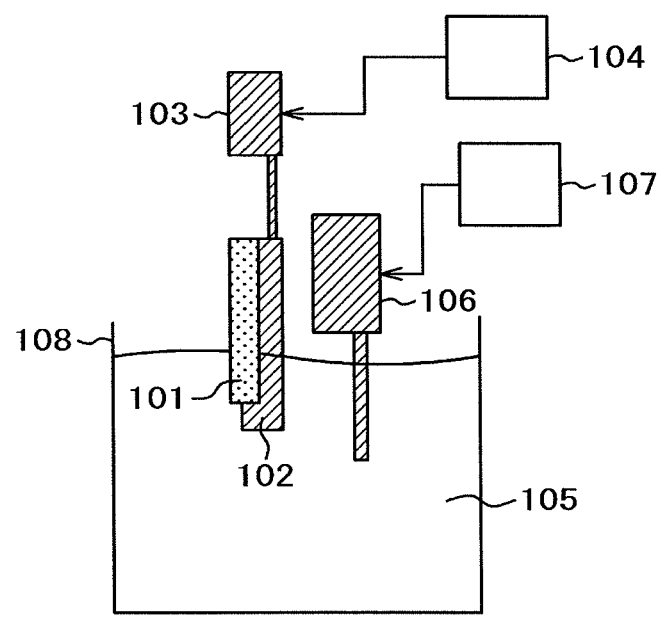
FIG. 16 is a block diagram of an exemplary observation specimen preparation device for an electron microscopic method according to a sixth embodiment of the present invention.

FIG. 16 is a block diagram of an observation specimen preparation device for an electron microscopic method according to the embodiment. The observation specimen preparation device for an electron microscopic method is configured of a sample 101, a sample supporting unit 102 that supports a sample, a drive unit 103 that freely moves up and down the sample supporting unit 102, the drive control unit 104 that controls the position and the rate of travel of the sample supporting unit 102, an ionic liquid adjusting unit 106 that fills an ionic liquid or an ionic liquid 105 mixed with a substance other than the ionic liquid in a liquid bath 108, and an ionic liquid adjustment control unit 107 that controls the adjustment of the ionic liquid or the ionic liquid 105 mixed with a substance other than the ionic liquid. It is noted that the configuration of the observation specimen preparation device for an electron microscopic method may be a configuration in which the device is installed on the sample chamber or the exhaust chamber of an electron microscope.

A method for applying an ionic liquid according to the embodiment will be described. In the embodiment, the sample 101 is an $SiO_2$ sample having line groove patterns, and the ionic liquid 105 is 1-Butyl-3-methylimidazolium bis(trifluoromethylsulfonyl)imide containing 95% of pure water. First, the sample 101 is supported on the sample supporting unit 102, the sample supporting unit 102 is lowered, and the sample 101 is put into the liquid bath 108 filled with the ionic liquid adjusted by the ionic liquid adjusting unit 106 beforehand. Subsequently, the sample supporting unit 102 is pulled up while controlling the rate of travel of the drive unit 103 by the drive control unit 104, and the ionic liquid 105 is applied to the sample 101. The rate of travel of the drive unit 103 is controlled, so that the film thickness of the ionic liquid 105 can be controlled. In the embodiment, the velocity of pulling up the sample supporting unit 102 from the liquid bath 108 was controlled at 5 cm/min, and the ionic liquid 105 was applied over the thin film. After that, the sample 101 was placed in the exhaust chamber for air purge. Pure water contained in the ionic liquid is vaporized by air purge, and the ionic liquid can be formed into a thin film. In the embodiment, vacuum exhaust was performed until the pressure of the exhaust chamber reached a pressure of $2 \times 10^{-2}$ Pa. It was shown that the film thickness of the ionic liquid 105 formed on the sample 101 was 100 monolayers by the method for measuring the film thickness according to the second embodiment. With the use of the observation specimen preparation device for an electron microscopic method according to the embodiment, it is possible to highly accurately control the film thickness of the ionic liquid on the sample.

Seventh Embodiment

In this embodiment, an observation specimen preparation device for an electron microscopic method will be described, which is in another configuration different from the method described in the third embodiment.

FIG. 17 is a block diagram of an observation specimen preparation device for an electron microscopic method according to the embodiment. The observation specimen preparation device for an electron microscopic method is configured of a sample 111, a sample supporting unit 112 that supports the sample 111, a heater 113, a temperature control unit 114, an ionic liquid film 115, a film supporting unit 116 that supports the ionic liquid film 115, a drive unit 117 that moves the film supporting unit 116, and a drive control unit 118. Here, the ionic liquid film is an ionic liquid in a plate shape or film shape. It is noted that the configuration of the observation specimen preparation device for an electron microscopic method may be a configuration in which the device is installed on the sample holder, the sample chamber, or the exhaust chamber of an electron microscope.

A method for applying an ionic liquid according to the embodiment will be described. In the embodiment, the sample 111 is an $SiO_2$ sample having line groove patterns. First, the sample 111 is supported on the sample supporting unit 112, the film supporting unit 116 is lowered while controlling the rate of travel of the drive unit 117 by the drive control unit 118, and the ionic liquid film 115 is brought into intimate contact with the sample 111. The temperature of the heater 113 is controlled by the temperature control unit 114 according to the type of the sample 111 and the type of the ionic liquid film 115, and an ionic liquid is applied to the sample 111. Since the viscosity of the ionic liquid is reduced at high temperature, the ionic liquid can be applied to the sample. In the embodiment, the temperature of the heater was controlled at a temperature of 60° C., and the ionic liquid was applied to the sample 111 while bringing the ionic liquid film 115 into intimate contact with the sample ill. It was shown by the method for measuring the film thickness according to the second embodiment that the film thickness of the formed ionic liquid on the sample 111 was one monolayer. With the use of the observation specimen preparation device for an electron microscopic method according to the embodiment, it is possible to highly accurately control the film thickness of the ionic liquid of the observation specimen by controlling the temperature of the heater.

Eighth Embodiment

Figure 18:
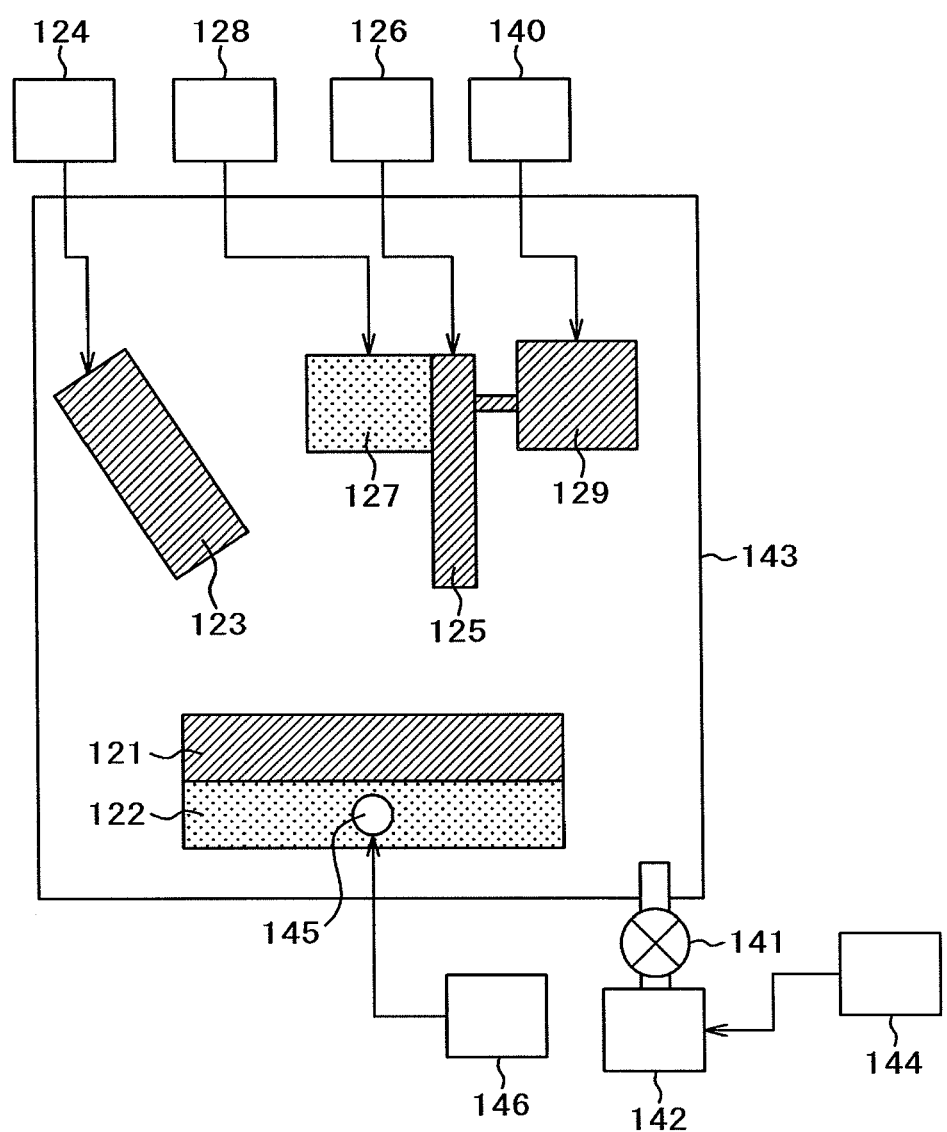
FIG. 18 is a block diagram of an exemplary observation specimen preparation device for an electron microscopic method according to an eight embodiment of the present invention.

In the embodiment, an observation specimen preparation device for an electron microscopic method will be described, which is in another configuration different from the method described in the third embodiment. In the embodiment, FIG. 18 is a block diagram of an observation specimen preparation device for an electron microscopic method according to the embodiment. The observation specimen preparation device for an electron microscopic method is configured of a sample 121, a sample supporting unit 122 that supports the sample, an ozone application source 123, an ozone application source control unit 124, an ionic liquid discharging unit 125, a discharge control unit 126, a driving mechanism 127 that moves the ionic liquid discharging unit 125, a drive control unit 128 that controls the position and rate of travel of the ionic liquid discharging unit 125, an ionic liquid adjusting unit 129 that mixes an ionic liquid with a substance other than the ionic liquid, an ionic liquid adjustment control unit 140 that controls the adjustment of the ionic liquid, a valve 141, an exhaust mechanism 142, an exhaust chamber 143, an exhaust control unit 144, a heater 145, and a temperature control unit 146. It is noted that the configuration of the observation specimen preparation device for an electron microscopic method may be a configuration in which the device is installed on the sample chamber or the exhaust chamber of an electron microscope.

A method for applying an ionic liquid according to the embodiment will be described. First, an ionic liquid or an ionic liquid mixed with a substance other than the ionic liquid at the ionic liquid adjusting unit 129 beforehand is prepared according to the sample 121. In the embodiment, since the sample 121 is an $SiO_2$ sample having line groove patterns, pure water was mixed in 1-Butyl-3-methylimidazolium Tetrafluoroborate to prepare a concentration of 1%. Subsequently, the application conditions for the ozone application source 123 are controlled by the ozone application source control unit 124 depending on the types of the sample 121 and the ionic liquid, and ozone is applied to the sample 121 supported on the sample supporting unit 122. Since the applied ozone improves the surface state on the sample 121, the wettability to the liquid is changed. In the embodiment, ozone was applied to the sample 121 for a second. After that, the amount of the ionic liquid discharged is controlled by the discharge control unit 126, and the ionic liquid is applied. In the embodiment, the ionic liquid was discharged by an ink jet method. Moreover, in order to prevent the solvent of the ionic liquid at one-percent concentration from being vaporized due to heat before discharging, the ionic liquid was discharged by a piezo method, not by a thermal method. The amount of the ionic liquid discharged per discharge depends on the nozzle diameter and the applied voltage, and can be controlled in the range of femtoliter to microliter. In the embodiment, the amount per discharge was set to two picoliters. Since the ionic liquid was coagulated in association with vaporization of the solvent when the number of discharges was 1,000 times or more, the number of discharges per place was set to 500 times. After that, similarly, the driving mechanism 127 is controlled by the drive control unit 128, the ionic liquid discharging unit 125 is moved, and the ionic liquid is applied. When the ionic liquid is applied or after the ionic liquid is applied, the temperature of the heater 145 is controlled by the temperature control unit 146, and the temperature of the sample 121 is adjusted depending on the type of the sample, the type of the ionic liquid, and the amount of discharge. The temperature of the sample 121 is adjusted to change the wettability between the sample and the ionic liquid, so that it is possible to form a state in which the form of the ionic liquid to be applied is advantageous to form a thin film. In the embodiment, the temperature of the sample 121 was set at a temperature of 40° C. when the ionic liquid was applied. After that, the exhaust mechanism 142 is controlled by the exhaust control unit 144, and the exhaust chamber 143 is subjected to vacuum exhaust. When the ionic liquid contains a substance that is vaporized under a vacuum, the substance that is vaporized under a vacuum is vaporized by vacuum exhaust, so that the ionic liquid can be formed into a thin film. In the embodiment, vacuum exhaust was performed until the pressure of the exhaust chamber 143 reached a pressure of $1\times10^{-4}$ Pa, which is almost the same vacuum degree in electron microscopic observation, and pure water was vaporized. With the use of the observation specimen preparation device for an electron microscopic method according to the embodiment, it is possible to highly accurately control the film thickness of the ionic liquid of the observation specimen by controlling the ozone application conditions, the adjustment of the ionic liquid, the control of the amount of the ionic liquid discharged, the temperature control of the sample, and the control of air purge. It is noted that in the embodiment, ozone is applied. However, ultraviolet rays or plasma may be applied.

REFERENCE SIGNS LIST

2 Sample
3 Liquid medium including an ionic liquid
5 Primary electron
6 Region to which a primary electron reaches
10 Electron source
11 Condenser lens
12 Diaphragm
13 Deflector
14 Objective lens
15 Sample stage
16 Sample holder
17 Sample
18 Detector
19 Pulse forming unit
20 Electron source control unit
21 Condenser lens control unit
22 Deflection signal control unit
23 Detection signal processing unit
24 Image generating unit
25 Image display unit
26 SEM control unit
27 Manipulation interface
28 Ammeter
29 Substrate current analyzing unit
30 Pulse control unit
31 Detector control unit 32 Sample chamber
72 Ionic liquid adjusting unit
73 Ionic liquid discharging unit
74 Sample
75 Sample holder
76 Sample holding unit
77 Sample holding unit rotating mechanism
80 Valve
81 Exhaust mechanism
82 Exhaust chamber
84 Ionic liquid adjustment control unit
85 Discharge control unit
86 Rotation control unit
87 Exhaust control unit
91 Acceleration voltage dependence of the secondary electron emission yield of a resist
92 Acceleration voltage dependence of the secondary electron emission yield of an ionic liquid
101 Sample
102 Sample supporting unit
103 Drive unit
104 Drive control unit
105 Ionic liquid or ionic liquid mixed with a substance other than the ionic liquid
106 Ionic liquid adjusting unit
107 Ionic liquid adjustment control unit
108 Liquid bath
111 Sample
112 Sample supporting unit
113 Heater
114 Temperature control unit
115 Ionic liquid film
116 Film supporting unit
117 Drive unit
118 Drive control unit
121 Sample
122 Sample supporting unit
123 Ozone application source
124 Ozone application source control unit
125 Ionic liquid discharging unit
126 Discharge control unit
127 Driving mechanism
128 Drive control unit
129 Ionic liquid adjusting unit
130, 131, 132 Window
140 Ionic liquid adjustment control unit
141 Valve
142 Exhaust mechanism
143 Exhaust chamber
144 Exhaust control unit
145 Heater
146 Temperature control unit

The invention claimed is:
1. An electron microscope comprising:
an electron source configured to emit a primary electron;
a sample holder configured to hold a sample;
an exhaust chamber on which the sample holder is placed and configured to exhaust air;
a lens system configured to focus the primary electron on the sample;
a deflector configured to scan the primary electron;
a detector configured to detect a secondary electron emitted from the sample by the primary electron;
an image generating unit configured to form an image using the secondary electron;
a sample chamber on which the sample holder is placed;
a measuring mechanism configured to measure a film thickness of a liquid medium, including an ionic liquid in a thin film shape or in a mesh film shape on the sample, using electrons; and
an irradiation condition control unit for the primary electron based on the film thickness of the liquid medium including an ionic liquid on the sample.

2. The electron microscope according to claim 1, wherein the measuring mechanism configured to measure a film thickness of the liquid medium including an ionic liquid includes:
a pulse forming unit configured to form a pulse electron that the primary electron is pulsed;
a secondary electron signal analyzing unit configured to analyze a secondary electron emission yield from a secondary electron signal emitted from the sample by the pulse electron; and
a secondary electron emission yield analyzing unit configured to analyze a primary electron acceleration voltage dependence of the secondary electron emission yield.

3. The electron microscope according to claim 2, wherein the measuring mechanism configured to measure a film thickness of the liquid medium uses the secondary electron emission yield compiled into a database.

4. The electron microscope according to claim 1, wherein the measuring mechanism configured to measure a film thickness of the liquid medium including an ionic liquid includes:
a substrate current measuring unit configured to measure a substrate current induced when the primary electron is irradiated to the sample; and
a substrate current analyzing unit configured to analyze a primary electron acceleration voltage dependence of the substrate current.

5. The electron microscope according to claim 1, wherein an applying unit configured to apply the liquid medium including an ionic liquid to an observation surface of the sample is included on the sample holder or the sample chamber on which the sample is held.

6. The electron microscope according to claim 5, wherein a mechanism configured to form the liquid medium including an ionic liquid applied on the sample into a thin film is included on the sample holder or the sample chamber on which the sample is held.

7. The observation specimen electron microscope according to claim 1, wherein: a thickness of a single molecular layer of the ionic liquid is one monolayer; and a film thickness of a portion to which the liquid medium including an ionic liquid is applied is one monolayer or more and 100 monolayers or less.

8. An electron microscopic method comprising the steps of:
measuring a film thickness of a liquid medium, including an ionic liquid in a thin film shape or in a mesh film shape on a sample, using electrons;
controlling an irradiation condition for a primary electron based on the film thickness of the liquid medium including an ionic liquid; and
irradiating a primary electron under the irradiation condition for the primary electron and imaging a form of the sample.

9. The electron microscopic method according to claim 8, further comprising the steps of:
applying the liquid medium including an ionic liquid to an observation surface of the sample; and
forming the liquid medium including an ionic liquid on the sample into a thin film.

10. The electron microscopic method according to claim 9, wherein the method performs, for a plurality of times, the steps of:
- applying the liquid medium including an ionic liquid to the observation surface of the sample;
- forming the liquid medium including an ionic liquid on the sample into a thin film; and
- measuring the film thickness of the liquid medium including an ionic liquid.

11. The electron microscopic method according to claim 8, wherein the step of measuring the film thickness of the liquid medium including an ionic liquid includes the steps of:
- irradiating a pulse electron to an observation surface of the sample;
- detecting a secondary electron signal emitted from the pulse electron; and
- analyzing a primary electron acceleration voltage dependence of a secondary electron emission yield from the secondary electron signal.

12. The electron microscopic method according to claim 8, wherein the step of measuring the film thickness of the liquid medium including an ionic liquid includes the steps of:
- measuring a substrate current induced when a primary electron is irradiated to an observation surface of the sample; and
- analyzing a primary electron acceleration voltage dependence of the measured substrate current.

13. The electron microscopic method according to claim 8, wherein:
- a thickness of a single molecular layer of the ionic liquid is one monolayer; and
- a film thickness of a portion to which the liquid medium including an ionic liquid is applied is one monolayer or more and 100 monolayers or less.

14. An observation specimen for an electron microscopic method comprising:
- a sample; and
- a liquid medium including an ionic liquid in a thin film shape or in a mesh film shape on the sample,
- wherein a thickness of a single molecular layer of the ionic liquid is one monolayer, and a film thickness of a portion to which the liquid medium, including an ionic liquid, is applied is one monolayer or more and 100 monolayers or less.

15. An observation specimen preparation device that prepares the observation specimen according to claim 14, the device comprising:
- an exhaust chamber;
- an exhaust mechanism;
- an applying unit configured to apply the liquid medium including an ionic liquid to an observation surface of a sample;
- a mechanism configured to form the liquid medium including an ionic liquid on the sample into a thin film; and
- a measuring mechanism configured to measure a film thickness of the liquid medium including an ionic liquid.

16. The observation specimen preparation device according to claim 15, wherein the measuring mechanism configured to measure a film thickness of the liquid medium including an ionic liquid includes:
- an electron source configured to emit a primary electron;
- a substrate current measuring unit configured to measure a substrate current induced when the primary electron is irradiated to the sample; and
- a substrate current analyzing unit configured to analyze a primary electron acceleration voltage dependence of the substrate current.

17. The observation specimen preparation device according to claim 15, wherein the measuring mechanism configured to measure a film thickness of the liquid medium including an ionic liquid includes:
- a pulse electron irradiating unit configured to irradiate a pulse electron to the observation surface of the sample;
- a detector configured to detect a secondary electron signal emitted from the pulse electron; and
- a secondary electron emission yield analyzing unit configured to analyze a primary electron acceleration voltage dependence of a secondary electron emission yield from the detected secondary electron signal.

* * * * *